Figure 1:
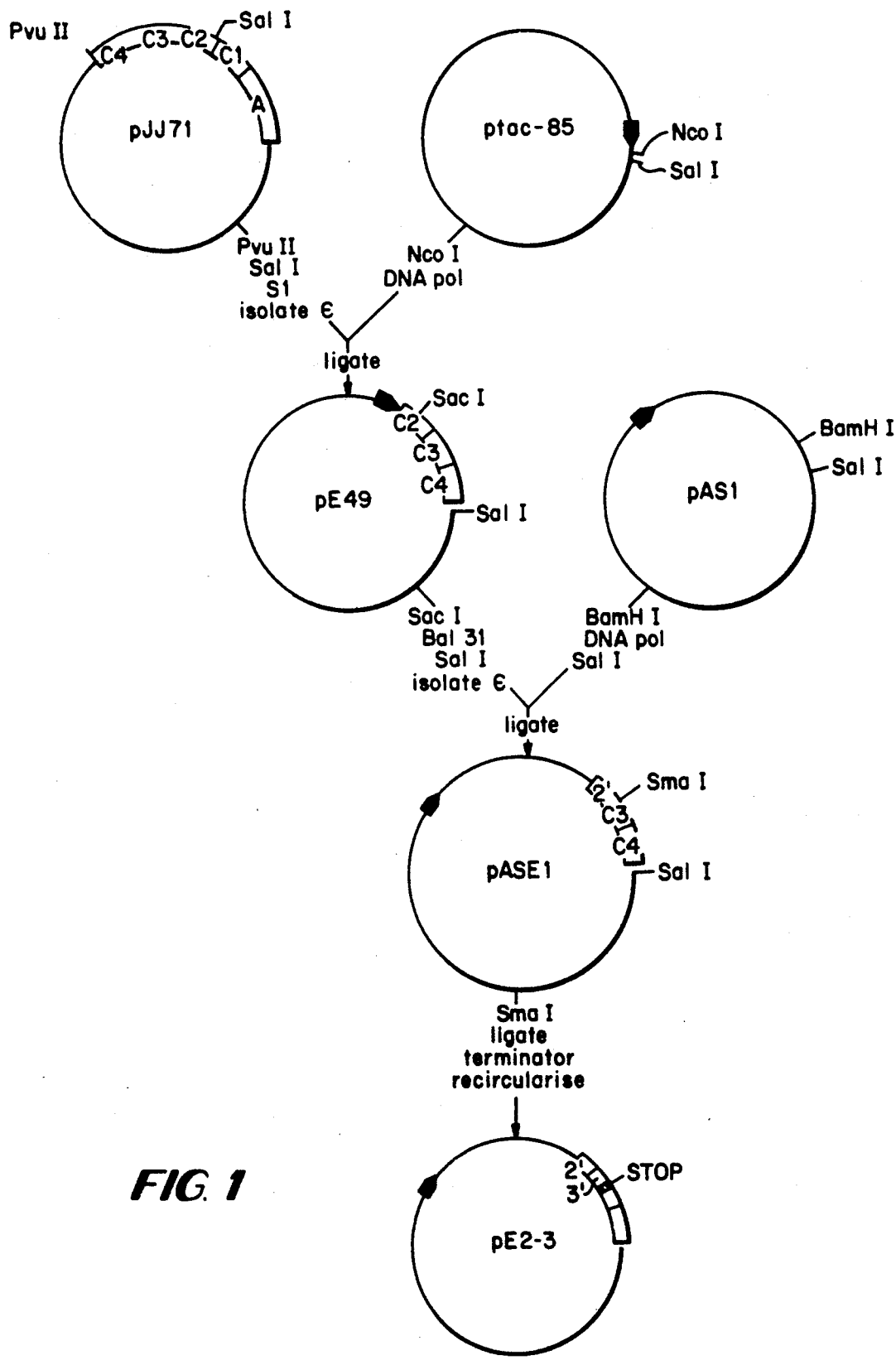

United States Patent [19]

Gould et al.

[11] Patent Number: 5,180,805
[45] Date of Patent: Jan. 19, 1993

[54] POLYPEPTIDE COMPETITOR FOR IMMUNOGLOBULIN E

[75] Inventors: Hannah J. Gould, London; Birgit A. Helm, Loughton, both of England

[73] Assignee: Research Corporation Limited, London, England

[21] Appl. No.: 730,530

[22] PCT Filed: Jul. 2, 1987

[86] PCT No.: PCT/GB87/00466

§ 371 Date: Feb. 24, 1989

§ 102(e) Date: Feb. 24, 1989

[87] PCT Pub. No.: WO88/00204

PCT Pub. Date: Jan. 14, 1988

Related U.S. Application Data

[63] Continuation of Ser. No. 295,033, Feb. 24, 1989, abandoned.

[30] Foreign Application Priority Data

Jul. 2, 1986 [GB] United Kingdom ............... 8616166

[51] Int. Cl.$^5$ ............................................. C07K 13/00
[52] U.S. Cl. ............................... 530/324; 530/388.22; 530/387.1; 530/862; 435/69.1; 536/23.53; 536/867
[58] Field of Search ................. 530/324, 387; 435/69.1

[56] References Cited

U.S. PATENT DOCUMENTS 4,161,522  7/1979  Hamburger .
4,171,299  10/1979  Hamburger .

OTHER PUBLICATIONS

Geha et al. (1985) "Inhibition of the Prausnitz-Kustner reaction by an immunoglobulin –chain fragment synthesized in E. coli." Nature (London) 315: 577–578.

Bennich et al. (1977) "Failure of the putative IgE pentapeptide to compete with IgE for receptors on basophils and mast cells." Int. Archs. Allergy Appl. Immun. 53: 459–468.

Gergely et al. (1984) "Localization of IgG Fc fragment epitopes which are responsible for antibody–dependent cellular cytotoxicity." Soviet immunology 5: 39–43.

Conrad et al, J. of Immunology 132(2): 796–803 (1984).

Primary Examiner—David L. Lacey
Assistant Examiner—Shelly J. Guest
Attorney, Agent, or Firm—Nixon & Vanderhye

[57] ABSTRACT

A competitor for human Immunoglobulin E (IgE) comprises a polypeptide which has a core sequence of seventy-six amino acids which is shown, together with the corresponding DNA sequence coding therefor, in FIG. 2. This amino acid sequence, numbered 1 to 76, corresponds to amino acids 301 to 376 of the epsilon heavy cain of IgE. The polypeptide may also include additional short sequences at the beginning and/or end of the core sequence which are physiologically harmless and do not contribute to the ability of the core sequence to bind compete with native IgE for the high-affinity receptor sites on human cells. The polypeptide is indicated for the treatment of Type I hypersensitivity reactions such as hay fever. The polypeptide may be produced synthetically or by expression from Escherichia coli containing a plasmid having a DNA segment coding for the polypeptide.

8 Claims, 2 Drawing Sheets

FIG. 2

| | | |
|---|---|---|
| 1 | (X)-Gln-Lys-His-Trp-Leu-Ser-Asp-Arg-Thr-Tyr- | |
| 1 | CAG AAG CAC TGG CTG TCA GAC CGC ACC TAC | |
| | | |
| 11 | Thr-Cys-Gln-Val-Thr-Tyr-Gln-Gly-His-Thr- | |
| 31 | ACC TGC CAG GTC ACC TAT CAA GGT CAC ACC | |
| | | |
| 21 | Phe-Glu-Asp-Ser-Thr-Lys-Lys-Cys-Ala-Asp- | |
| 61 | TTT GAG GAC AGC ACC AAG AAG TGT GCA GAT | |
| | | |
| 31 | Ser-Asn-Pro-Arg-Gly-Val-Ser-Ala-Tyr-Leu- | |
| 91 | TCC AAC CCG AGA GGG GTC AGC GCC TAC CTA | |
| | | |
| 41 | Ser-Arg-Pro-Ser-Pro-Phe-Asp-Leu-Phe-Ile- | |
| 121 | AGC CGG CCC AGC CCG TTC GAC CTG TTC ATC | |
| | | |
| 51 | Arg-Lys-Ser-Pro-Thr-Ile-Thr-Cys-Leu-Val- | |
| 151 | CGC AAG TCG CCC ACG ATC ACC TGT CTG GTC | |
| | | |
| 61 | Val-Asp-Leu-Ala-Pro-Ser-Lys-Gly-Thr-Val- | |
| 181 | GTC GAC CTG GCA CCC ACC AAG GGG ACC GTG | |
| | | |
| 71 | Asn-Leu-Thr-Trp-Ser-Arg-(Y) | |
| 211 | AAC CTG ACC TGG TCC CGG | |

POLYPEPTIDE COMPETITOR FOR IMMUNOGLOBULIN E

This is a continuation of application Ser. No. 07/295,033 filed Feb. 24, 1989, now abandoned.

This invention relates to a polypeptide competitor for human Immunoglobulin E (IgE). More particularly the invention relates to a polypeptide which is capable of binding specifically to the high affinity Fc receptor sites for IgE which exist on human cells, particularly on mast cells and basophils, thereby inhibiting the biological responses, such as exocytosis or degranulation, which take place when antigen specific IgE binds to and cross-links such receptor sites in the presence of antigen. The invention also relates to pharmaceutical preparations in which the polypeptide is an active constituent. The invention further relates to a method for the preparation of the polypeptide using genetically modified bacteria.

In the human immune system, the principal role of IgE is believed to be to provide immunity to parasites. It also, however, mediates Type I hypersensitivity which is an allergic response leading to the manifestation of such symptoms as hay fever and asthma. Briefly, the mechanism of the allergic response is that on encountering a normally innocuous antigen such as pollen, synthesis of antigen-specific IgE by B-cells is initiated. The antigen-specific IgE then binds to mast cell receptor sites via its Fc region and thereafter any further encounter with the antigen triggers degranulation of the mast cells releasing mediators, principally histamine, resulting in the acute inflammatory symptoms typical of Type I hypersensitivity.

Structurally, IgE, in common with the other immunoglobulins, comprises two heavy and two light chains, the epsilon heavy chain having five domains, a variable domain VH and constant domains CH1 to CH4. The molecular weight of IgE is in the region of 188,000 of which the heavy chain accounts for about 72,500, representing a sequence of approximately 550 amino acid residues.

It has been reported (Nature, vol.315, 1985, No.6020, pp 577–578) that a peptide sequence of 330 amino-acids corresponding to amino acid residues 218 to 547 (in accordance with the numbering given by Bennich, Progress in Immunology II, Vol I, July 1974, pp 49–58) of the epsilon heavy chain of IgE has an inhibitory effect on the release of mediators from human mast cells. The numbering is erroneously assigned in that paper in Nature; the more correct numbering would be 208 to 537. The 330 amino-acid sequence exists as a dimer consisting of two chains of amino-acids, each of 330 amino-acids in length, linked by disulphide bonds.

U.S. Pat. Nos. 4,171,299 and 4,161,522 disclose that an oligopeptide containing from three to ten amino acids in a sequence selected from a portion of amino acids 265 to 537 of the Bennich nomenclature (see reference above) of the Fc region of human IgE will block Fc receptors of mast cells thus inhibiting degranulation and release of mediators such as histamine. The most active of these oligopeptides is identified as the pentapeptide Asp-Ser-Asp-Pro-Arg (called HEPP: Human Immunoglobulin E Polypeptide) derived from the amino acid sequence 320 to 324 of the IgE heavy chain. In native IgE amino acid 322 is asparagine, but it is suggested in the Patents that substitution of asparagine by aspartic acid leads to a substantial enhancement of the blocking activity.

In the Patents mentioned above the full sequence which is attributed to Bennich (Progress in Immunology II, Vol I, July 1974, pp 49–58) is quoted and shows aspartic acid at location 322. However, Bennich himself later asserts (Int. Arch. Allergy Appl. Immunol. 53, 459) that asparagine resides at that location. Bennich also reports that neither of the peptides Asp-Ser-Asp-Pro-Arg nor Asp-Ser-Asn-Pro-Arg has any blocking activity. Determination of the gene sequence has shown that amino acid 322 is asparagine and not aspartic acid. In European Patent Application No. 102634 asparagine and not aspartic acid is correctly quoted at the equivalent location.

Further, it is also reported that the specific activity of HEPP is low requiring excessively large doses for any significant physiological effect.

It is knwon that IgE epsilon chain fragments may be synthesised in *Escherichia coli* by cloning and expression of the DNA sequences coding for the appropriate domains of the IgE chain (Eur. J. Immunol. 1985, 15: 966-969 and Proc. Natl. Acad. Sc. USA, vol.81, 1984, 2955-2959).

An object of the present invention is to provide a new peptide for use in anti-allergy treatment.

According to the present invention there is provided a polypeptide competitor for human Immunoglobulin E (IgE), comprising a monomeric chain of amino acids having the having following sequence:

Gln-Lys-His-Trp-Leu-Ser-Asp-Arg-Thr-Tyr-
Thr-Cys-Gln-Val-Thr-Tyr-Gln-Gly-His-Thr-
Phe-Glu-Asp-Ser-Thr-Lys-Lys-Cys-Ala-Asp-
Ser-Asn-Pro-Arg-Gly-Val-Ser-Ala-Tyr-Leu-
Ser-Arg-Pro-Ser-Pro-Phe-Asp-Leu-Phe-Ile-
Arg-Lys-Ser-Pro-Thr-Ile-Thr-Cys-Leu-Val-
Val-Asp-Leu-Ala-Pro-Ser-Lys-Gly-Thr-Val-
Asn-Leu-Thr-Trp-Ser-Arg

The core sequence of seventy-six amino acids defined above is capable of binding to human IgE high-affinity receptor sites. The said sequence, numbered in FIG. 2 as 1 to 76, corresponds to the amino acid sequence spanning residues 291 to 366 (Bennich nomenclature) of the heavy chain of human IgE.

In addition the core sequence may have short sequences of amino acids initiating (X—) and terminating (—Y) the core sequence and covalently attached to its 3' and/or 5' ends, which do not participate in the binding to IgE receptors and which are not physiologically harmful.

Further according to the invention there is provided a DNA having the following nucleotide sequence:

CAG AAG CAC TGG CTG TCA GAC CGC ACC TAC
ACC TGC CAG GTC ACC TAT CAA GGT CAC ACC
TTT GAG GAC AGC ACC AAG AAG TGT GCA GAT
TCC AAC CCG AGA GGG GTC AGC GCC TAC CTA
AGC CGG CCC AGC CCG TTC GAC CTG TTC ATC
CGC AAG TCG CCC ACG ATC ACC TGT CTG GTC
GTC GAC CTG GCA CCC ACC AAG GGG ACC GTG
AAC CTG ACC TGG TCC CGG.

The present invention also provides a transformant in which the DNA contains the nucleotide sequence defined above. Preferably the transformant host is *Escherichia coli*

Most preferably the transformant comprises *Escherichia coli* N4830 harbouring the plasmid pE 2-3 (Accession Number NCTC 11993, deposited with the National Collection of Type Cultures, London on Jul. 1st. 1986).

The invention further provides a vector in which the DNA is as defined above, said segment being oriented within said vector such that in a host said segment is expressed to produce a polypeptide. The invention also provides a host organism transformed by the aforesaid vector.

Further according to the present invention there is provided a method of preparing the polypeptide defined above, comprising culturing the aforesaid host organism and isolating the polypeptide from the culture.

Using this method the resultant polypeptide product may include the groups X and Y defined above. If thought necessary or desirable these groups may be removed from the core sequence of amino acids by standard degradation procedures but, being physiologically harmless, there is no compelling reason for removing them. In the specific example which will be given later, the group represented by X is $NH_2$-Met-Asp- and the group represented by Y is -Leu-Ile-Asn.

Alternatively the polypeptide may be synthesised by known chemical synthetic methods.

This invention also includes a pharmaceutical preparation in which the active principle is the polypeptide defined above.

The preparation may also include a pharmaceutical carrier permitting administration of the polypeptide in an appropriate manner, for example intranasally.

The polypeptide of the invention may also be covalently linked to or associated with other therapeutic or diagnositic agents or other molecules with the effect that the polypeptide acts to target the therapeutic or diagnostic agent to cells bearing IgE high-affinity receptors.

By way of explanation, the core sequence of the polypeptide of this invention bridges the second and third domains of the epsilon chain constant region of IgE. Previous work (J. Immunol 114, 1838, 1975; Immunol. Rev. 41, 3, 1978) concluded that both the second and fourth domains were required to form the binding site. It was therefore unexpected that in respect of polypeptides with a major deletion in the CH2 domain, a major deletion in the CH3 domain and deletion of the entire CH4 domain or a combination of these deletions a binding ability comparable to that of native IgE would result.

That the monomeric polypeptide of the invention has the ability to bind to the high-affinity receptors of mast cells and basophils is quite surprising. Firstly, the fact that the chain is monomeric at all is unexpected since it would have been anticipated that after synthesis of the peptide chain there would be an immediate spontaneous dimerisation of peptide chains via their cysteines at location 318 (28 in FIG. 2). The cysteines at locations 231 and 318 have been previously implicated in the formation of the inter-epsilon chain disulphide bonding in IgE. The surprising existence of the monomeric polypeptide of this invention which includes the cysteine at location 318 suggests that one explanation of this unexpected occurrence is that the inter epsilon chain disulphide pairing in IgE is not, as previously believed, of the homotypic (AA,BB) type but of the heterotypic (2AB) type. Secondly, the binding activity of the monomeric polypeptide is quite unexpected since it has previously been believed that two epsilon chains were necessary for the binding at mast cell receptor sites to trigger exocytosis. In the same study, loss of binding activity was found to occur when the inter epsilon chain bonding at location 318 was broken even although the chains remained covalently linked via the more resistant disulphide interchain bond assumed to link the two cysteines at location 241. The polypeptide of the invention lacks sequences necessary for the formation of any of the three immunoglobulin domains which exist in human IgE and thus this invention indicates that this dimeric structural framework is not essential in its entirety for recognition by the high affinity receptors of the mast cells.

The core sequence of the invention is less than a quarter of the size of the Fc region of the IgE heavy chain, having a molecular weight of around 10,000. The amino acid sequence of the polypeptide spans the C-terminal end of the CH2 domain and the N-terminal end of the CH3 domain and incorporates a beta-turn from each of the two domains and the so-called "hinge" between them.

A method for producing the polypeptide utilising genetically modified *Escherichia coli* containing a DNA insert coding for the core amino acid sequence will now be described in the following Example 1.

EXAMPLE 1

Human myeloma cell line 266B1 which had previously been used by Bennich (Prog. in Immunol. Vol I, North Holland Publishing Company, pages 49 to 58, 1974) contains a functional epsilon gene sequence that can easily be cloned.

The known amino acid sequence of IgE provided all the information required to make an oligonucleotide probe for screening a cDNA library from the 266B1 cell line. The original cell line synthesised from 2 to 7 micrograms of IgE per $10^6$ cells per 48 hours. During propagation of the line and adaptation to growth in suspension culture, the synthesis of IgE had evidently declined, the levels obtained being about 20 nanograms of IgE per $10^6$ cells per 48 hours. The synthesis of IgE was confirmed by labelling the protein in culture and SDS polyacrylamide gel electrophoresis of the fraction precipititated from the culture supernatants by anti-human IgE Fc anti-serum. Similar analysis of the fraction precipitated by anti- human lambda light chain antiserum demonstrated the presence of a twenty-fold excess of monomeric over IgE-associated lambda light chain in the secreted immunoglobulin. Despite the poor expression of the epsilon gene in 266B1, the level of mRNA was sufficient for the task of cDNA synthesis and cloning.

Total RNA was extracted from 266B1 cells and mRNA was purified by oligo-dT chromatography. The presence of intact epsilon chain mRNA was demonstrated by translation into polypeptide chains immunoprecipitable by goat anti-human IgE and having the expected electrophoretic mobility in SDS polyacrylamide gels corresponding to the 66,000 dalton unglycosylated human epsilon chain. The epsilon chain mRNA was enriched by a factor of ten by sucrose gradient centrifugation, the relative concentrations of epsilon chain mRNA in the different fractions being monitored both by the translation assay and by oligonucleotide-primed synthesis of cDNA of the expected length.

Double-stranded cDNA was enzymatically synthesised using routine procedures and the cDNA was recombined by means of linkers into a appropriate restriction site in a plasmid vector and transformed into E. coli.

An oligonucleotide probe of eleven nucleotides was designed on the basis of the amino acid sequence of the protein previously determined by conventional amino acid sequencing techniques and was chemically synthesised. The probe itself failed to detect any cDNA clones but served as a satisfactory primer for cDNA synthesis, permitting the acquisition of additional sequence information by DNA sequencing. A new 22 nucleotide-long probe was constructed, based on this sequence and the larger probe detected five positive cDNA clones out of a total of 500. The cDNA inserts of the positive clones were excised by digestion with the appropriate restriction endonuclease and the sizes were found to be in the range of from 0.6 to 2.0 kb; only the largest, 2 kb clone, designated pJJ71, was extensively characterised. It contains the sequences correponding to the 5' and 3' untranslated regions of the mRNA, plus those encoding the amino terminal secretion peptide of twenty amino acids and the entire mature epsilon chain.

Reference is now made to the accompanying drawing which shows the derivation of the plasmid pE2-3, the expression plasmid directing the synthesis of the polypeptide of the invention. The human epsilon DNA coding sequence is represented by the box V indicating the variable region, and C1 to C4, the four constant domains. The solid arrows denote the inducible promoters mediating transcription of sequences cloned downstream. In ptac-85 and its derivative pE49 the tac promoter is present: the lambda P1 promoter is used by vector pAS1 and recombinants pASE1 and pE2-3. The synthetic DNA translation terminator in pE2-3 has the sequence 5'-GCTTAATTAATTAAGC-3'.

Expression of the polypeptide in E. coli was achieved via three subclonings of epsilon Fc cDNA cloned in pJJ71. First, the SalI-PvuII fragment corresponding to epsilon Fc and some forty base pairs of untranslated sequences, after digestion with S1 nuclease, was ligated into the filled NcoI site of ptac-85. The resulting plasmid, pe49, directs the expression of epsilon Fc and introduces a unique SalI site at the 3' end of the truncated flanking sequences. Second, pe49, linearised by SacI and treated with the double stranded exonuclease Bal31, was recleaved by SalI and the DNA fragment corresponding to amino acids 291 to 537 of epsilon Fc was subcloned into pASI. The pASI had been treated with BamHI and SalI restriction enzymes (the BamHI site having been made blunt-ended using DNA polymerase) in order to have compatible termini to those bounding the fragment from pe49. The resulting plasmid pASe1 directed the synthesis of an epsilon fragment comprising the third and fourth domains and part of the second domain from amino acid 291. Third, the expression product of pASE1 was foreshortened at its carboxy terminus by introducing a translation termination signal into the cloned DNA at a SmaI site in the position corresponding to amino acid 365. The construct, pE2-3, was generated by blunt ligation of a synthetic DNA fragment which contains translational stop codons in all three reading frames to pASE1 DNA linearised with SmaI.

The polypeptide of the invention was obtained when E. coli strain N4830 harbouring pE2-3 was grown under inducing conditions. Expression is controlled by the lambda cI repressor which shuts off transcription from the lambda PL promoter. E. coli strain N4830 contains a thermolabile cI repressor which is active at 30 degrees and inactive at 42 degrees Centigrade. A culture of N4830/pE2-3 was thus grown under non-inducing conditions at 30 degrees Centigrade to an $A_{600}$ of 0.8 then heat-shocked at this density by addition of an equal volume of medium preheated to 65 degrees Centigrade. After repressor inactivation the culture was grown at 42 degrees Centigrade for a further three hours and then harvested. Electrophoresis of a lysate of this culture showed the presence of a 10K peptide (not present in the absence of induction) visible on Coomassie staining, and shown immunologically to be an epsilon derivative by Western blotting. The expected size of the product of the gene fragment is 9,500 daltons.

The polypeptide was present in the lysate as insoluble material which was recovered by dissolution in 8M urea. The peptide remained soluble after removal of urea by dialysis and was purified to near homogeneity by anti-human epsilon affinity chromatography. Polyacrylamide gel electrophoresis under non-reducing (as well as reducing) conditions showed that the purified polypeptide had a molecular weight of about 10,000, indicating that unreduced peptide was monomeric.

EXAMPLE 2

The effectiveness of the polypeptide of the invention was compared with natural IgE and various fragments thereof in a series of tests using the passive cutaneous anaphylaxis (PCA) reaction [described in Nature 315: 577-578 (1985)]. The results are presented below in Table I.

TABLE I

| Source | Amino acids | Heavy-chain Domains | | | | | Activity |
|---|---|---|---|---|---|---|---|
| | | VH | CH1 | CH2 | CH3 | CH4 | |
| Myeloma IgE (PS) | 1-457 | + | + | + | + | + | + |
| pSC213 | 208-537 | − | − | + | + | + | + |
| pES1 | 300-537 | − | − | p | + | + | + |
| PE delta 4 | 209-429 | − | − | + | + | − | ± |
| pE2-3 | 291-366* | − | − | p | p | − | + | p = part of domain
*amino acid sequence 1 to 76 shown in FIG. 2

The approach to intervention in the allergic response adopted in the present invention is to block IgE high affinity receptor sites by administration to the patient of an amount of the polypeptide of the invention. This approach is believed to leave the low-affinity receptors unaffected and free to participate in their apparent immunological role.

From the results summarised in Table I, it can be seen that a positive effect is attained with all the sequences quoted, thus narrowing down the binding sites of IgE to mast cells to the seventy-six amino acid sequence of this invention. This sequence displayed an affinity constant for the human basophil receptor (5 × $10^9$/mol) which was indistinguishable from that of a myeloma IgE.

Inhibition of the Prausnitz-Kustner reaction was also displayed by the fragments listed in Table 1 above, that is, by amino acid sequences which contain the sequence 1 to 76 shown in FIG. 2, but, no inhibition was found for three other fragments of IgE, namely:
  (i) amino acids spanning locations 430 to 537 of the IgE sequence, and therefore containing no residues in common with the polypeptide of the invention, (ii) amino acids spanning residues 208 to 326, and therefore containing the residues 1 to 35 of the polypeptide of this invention; and,
(iii) amino acids spanning residues 329 to 537, and therefore containing the residues 38 to 76 of the polypeptide of this invention.

The results of the P-K reaction tests were as follows:

Inhibition of the P-K Reaction by IgE Fragments

A single subject was used for passive sensitisation. The serum IgE of this subject was 4 IU/ml (approximately 10 ng/ml). The sensitising serum (E.C.) contained 380 IU/ml of IgE (912 ng/ml serum E.C.), of which 8.7% was directed against ragweed antigen, as determined by the specific drop in serum IgE following absorption of the serum over a Sepharose 4B ragweed antigen column compared with a control Sepharose 4B human serum albumin. Serum E.C. was free of detectable hepatitis B antigen and of antibodies to that antigen and to human immunodeficiency virus (HIV). Serum E.C. was obtained in 1983 and its donor is currently (1987) healthy and HIV antibody negative. Epsilon chaim fragments were injected into skin sites one hour before the injection of serum E.C. Skin sites were challenged 48 hours later with ragweed antigen (1,000 protein nitrogen units/ml of a mixture of giant and short ragweed). Twenty minutes later the skin sites were examined for the presence of wheal and erythema. The surface area of the reaction was estimated as follows: Transparent tape was used to transfer the outline for the reactions to paper which was then cut out and weighed on an analytical balance. The area was read from a standard curve. All injections were intradermal and 0.02 ml in volume. In each experiment a set of skin sites was also sensitised with diluent. None of these sites showed wheal or flare when challenged with ragweed antigen. The diluent consisted of 0.15M sodium chloride and 0.03% human serum albumin. In both experiments, reported in Table 2 below, skin sites were sensitised with a 1:100 dilution of serum E.C. containing $5 \times 10^{-11}$M IgE.

TABLE 2

| Inhibitor | Area of Wheal & Flare | |
|---|---|---|
| | Expt. 1 10 ug/ml | Expt. 2 1 ug/ml |
| Diluent | 65/380 | 92/455 |
| IgE (P.S.) | 0/0 | 0/0 |
| aa 208-537 | 0/0 | 0/0 |
| aa 291-537 | 0/0 | 0/0 |
| aa 209-429 | 0/0 | 0/0 |
| aa 291-366* | 0/0 | 0/0 |
| aa 430-537 | 60/416 | 85/438 |
| aa 208-326 | 70/350 | 80/405 |
| aa 329-537 | 69/375 | 78/398 |

* = aa 1 to 76 in FIG. 2.

Relative Activity of Recombinant IgE (ND) Peptides in the Inhibition of the P-K Reaction The molarities of the epsilon chain fragments were calculated taking into account the proportion of dimers versus monomers in each preparation. Monomers were included in the calculations because the polypeptide of the invention has never existed in detectable dimeric or oligomeric forms and it was a potent inhibitor of the P-K reaction (see Table 2 above). Each fragment was used over a range of $10^{-13}$ to $10^{-6}$M in ten-fold increments. The results are presented in Table 3 below.

TABLE 3

| | Molarity required for 50% inhibition of the P-K reaction reduced by | | | |
|---|---|---|---|---|
| | Expt 1 Serum E.E. dil 1:100 = $5 \times 10^{-11}$M IgE | | Expt 2 Serum E.C. dil 1:20 = $2.5 \times 10^{-10}$M IgE | |
| Source | Molarity | % Potency | Molarity | % Potency |
| IgE (P.S.) | $2 \times 10^{-10}$ | 100 | $2 \times 10^{-9}$ | 100 |
| aa 208-537 | $4 \times 10^{-10}$ | 50 | $4 \times 10^{-9}$ | 50 |
| aa 291-537 | $5 \times 10^{-10}$ | 40 | $4 \times 10^{-9}$ | 50 |
| aa 209-429 | $5 \times 10^{-10}$ | 40 | $6 \times 10^{-9}$ | 33 |
| aa 291-366* | $6 \times 10^{-10}$ | 33 | $5 \times 10^{-9}$ | 40 |

* = 1 to 76 in FIG. 2.

Duration of the Inhibition of the P-K Reaction

In Table 4 below, values are given in days elapsed following the injection of the inhibitor before a successful P-K reaction could be achieved. Multiple skin sites of a normal subject were injected at day 0 with IgE (P.S.) the polypeptide of the invention or diluent. At intervals (days 0,4,9,12,14,17,19,21) individual skin sites were sensitised with a 1:100 dilution of serum E.C. ($5 \times 10^{11}$M IgE) then challenged 48 hours later with ragweed antigen. Sites pretreated with diluent always gave a positive wheal and flare reaction with a mean standard deviation of the flare of 392±58 mm for the eight successive determinations. The days shown in Table 4 represent the time of the first appearance of flare and/or erythema at the challenged skin sites.

TABLE 4

| Inhibitor | Inhibitor Concentration | |
|---|---|---|
| | $10^{-7}$M | $10^{-6}$M |
| IgE (P.S.) | 12 | 19 |
| aa 301-376* | 9 | 14 |

* = 1 to 76 in FIG. 2.

We claim:
1. A polypeptide which is capable of binding specifically to the high affinity Ec receptor sites for IgE which exists on human cells and which has the following amino acid sequence:
Gln-Lys-His-Trp-Leu-Ser-Asp-Arg-Thr-Tyr-Thr-Cys-Gln-Val-Thr-Tyr-Gln-Gly-His-Thr-Pha-Glu-Asp-Ser-Thr-Lys-Lys-Cys-Ala-Asp-Ser-Asn-Pro-Arg-Gly-Val-Ser-Ala-Tyr-Leu-Ser-Arg-Pro-Ser-Pro-Phe-Asp-Leu-Phe-Ila-Arg-Lys-Ser-Pro-Thr-Ile-Thr-Cys-Leu-Val-Val-Asp-Leu-Ala-Pro-Ser-Lys-Gly-Thr-Val-Asn-Leu-Thr-Trp-Ser-Arg.

2. A polypeptide which is capable of binding specifically to the high affinity Fc receptor sites for IgE which exists on human cells and which has the following amino acid sequence:
X-Gln-Lys-His-Trp-Leu-Ser-Asp-Arg-Thr-Tyr-Thr-Cys-Gln-Val-Thr-Tyr-Gln-Gly-His-Thr-Phe-Glu-Asp-Ser-Thr-Lys-Lys-Cys-Ala-Asp-Ser-Asn-Pro-Arg-Gly-Val-Ser-Ala-Tyr-Leu-Ser-Arg-Pro-Ser-Pro-Phe-Asp-Leu-Phe-Ile-Arg-Lys-Ser-Pro-Thr-Ile-Thr-Cys-Leu-Val-Val-Asp-Leu-Ala-Pro-Ser-Lys-Gly-Thr-Val-Asn-Leu-Thr-Trp-Ser-Arg- Y,
in which X and Y are oligopeptide sequences initiating and terminating the chain which do not prevent said polypeptide from binding specifically to the high affinity Fc receptor sites on human cells and are not physiologically harmful.

3. A method of preparing the polypeptide claimed in claim 2, said method comprising the steps of:
culturing a host transformed by a vector comprising a DNA segment having the following nucletide sequence:
CAG AAG CAC TGG CTG TCA GAC CGC ACC TAC
ACC TGC CAG GTC ACC TAT CAA GGT CAC ACC
TTT GAG GAC AGC ACC AAG AAG TGT GCA GAT
TCC AAC CCG AGA GGG GTC AGC GCC TAC CTA
AGC CGG CCC AGC CCG TTC GAC CTG TTC ATC
CGC AAG TCG CCC ACG ATC ACC TGT CTG GTC
GTC GAC CTG GCA CCC ACC AAG GGG ACC GTG
AAC CTG ACC TGG TCC CGG
said segment being oriented within said vector such that in a host said segment is expressed to produce a polypeptide; and
isolating the polypeptide from the culture.

4. A method of preparing the polypeptide, said method comprising the steps of:
culturing a host transformed by a vector comprising a DNA segment having the following nucleotide sequence:
CAG AAG CAC TGG CTG TCA GAC CGC ACC TAC
ACC TGC CAG GTC ACC TAT CAA GGT CAC ACC
TTT GAG GAC AGC ACC AAG AAG TGT GCA GAT
TCC AAC CCG AGA GGG GTC AGC GCC TAC CTA
AGC CGG CCC AGC CCG TTC GAC CTG TTC ATC
CGC AAG TCG CCC ACG ATC ACC TGT CTG GTC
GTC GAC CTG GCA CCC ACC AAG GGG ACC GTG
AAC CTG ACC TGG TCC CGG
isolating the polypeptide from the culture to obtain a polypeptide as claimed in claim 17; and
treating that polypeptide to remove the chain initiating and terminating groups X and Y.

5. In a conpetitive binding assay in which a competitor is used, the improvement being said competition is the polypeptide claimed in claim 1.

6. In a competitive binding assay in which a competitior is used, the improvement being said competitor is the polypeptide claimed in claim 2.

7. A diagnostic kit including means for conducting a competitive binding assay and including, for use as a competitor in said assay, a polypeptide as claimed in claim 1.

8. A diagnostic kit including means for conducting a competitive binding assay and including, for use as a competitor in said assay, a polypeptide as claimed in claim 2.

* * * * *